(12) United States Patent
Greager et al.

(10) Patent No.: US 7,728,178 B2
(45) Date of Patent: Jun. 1, 2010

(54) PRODUCTION OF DETERGENT RANGE ALCOHOLS

(75) Inventors: Ivan Philip Greager, Bromhof (ZA); James Christoffel Crause, Vaalpark (ZA)

(73) Assignee: Sasol Technology (Proprietary) Limited, Sasolburg (ZA)

( * ) Notice: Subject to any disclaimer, the term of this patent is extended or adjusted under 35 U.S.C. 154(b) by 0 days.

(21) Appl. No.: 11/996,894

(22) PCT Filed: Aug. 31, 2006

(86) PCT No.: PCT/IB2006/002380

§ 371 (c)(1),
(2), (4) Date: Jun. 12, 2008

(87) PCT Pub. No.: WO2007/026225

PCT Pub. Date: Mar. 8, 2007

(65) Prior Publication Data

US 2009/0203804 A1    Aug. 13, 2009

(30) Foreign Application Priority Data

Aug. 31, 2005 (ZA) .............................. 2005/06977
Aug. 31, 2005 (ZA) .............................. 2005/06978

(51) Int. Cl.
*C07C 45/50* (2006.01)
*C07C 29/14* (2006.01)

(52) U.S. Cl. ..................................... 568/451; 568/880

(58) Field of Classification Search ................. 568/451, 568/880

See application file for complete search history.

(56) References Cited

FOREIGN PATENT DOCUMENTS

| WO | WO2004058921 | * | 7/2004 |
| WO | WO 2004/080926 A2 | | 9/2004 |
| WO | WO 2005/037751 A2 | | 4/2005 |

OTHER PUBLICATIONS

International Search Report for PCT/IB2006/002379 published Jul. 12, 2007 as WO 2007/026225 A3.

* cited by examiner

*Primary Examiner*—Sikarl A Witherspoon
(74) *Attorney, Agent, or Firm*—Brinks Hofer Gilson & Lione

(57) ABSTRACT

This invention relates to a process for the production of aldehydes/alcohols and alkyl benzene. According to the invention, a hydrocarbon feed stream containing olefins and paraffins having an average number of carbon atoms from 10 to 18 per molecule, typically derived from the condensation product of a Fischer-Tropsch reaction is subjected to a hydroformylation reaction to provide a hydroformylation product containing aldehydes/alcohols and paraffins. An aldehyde/alcohol product is separated from the paraffins in the hydroformylation product to provide an aldehyde/alcohol product stream and a paraffin stream. The paraffin stream separated from the hydroformylation product is then subjected to a dehydrogenation reaction to form a dehydrogenation product containing olefins and paraffins, and the dehydrogenation product is subjected to an alkylation reaction to convert olefins to alkyl benzene.

14 Claims, 2 Drawing Sheets

PRODUCTION OF DETERGENT RANGE ALCOHOLS

CROSS REFERENCE TO RELATED APPLICATIONS

The present patent application is the National Stage of International Application No. PCT/IB2006/02380, filed Aug. 31, 2006, which claims the priority of South African Application No. 2005/06977, filed Aug. 31, 2005, and claims the priority of South African Application No. 2005/06978, filed Aug. 31, 2005.

BACKGROUND OF THE INVENTION

This invention relates to a process for the co-production of alcohols and alkyl benzenes, typically those in the detergent range.

Detergent range alcohols are alcohols, usually in the $C_8$ to $C_{20}$ range, (i.e. from 8 to 20 carbon atoms in the molecules) that are useful in the manufacture of detergents and surfactants.

Detergent range alcohols are commercially produced from the condensate product of a high temperature Fischer-Tropsch reaction, employing an iron based catalyst. Typically a feed stream consisting predominantly of olefins is recovered from such a Fischer-Tropsch reaction by distillation. The feed stream from the Fischer-Tropsch reaction is fractionated into a stream containing olefins in the 2C range, which is introduced to a hydroformylation reactor in which the olefins are converted to aldehydes (in the case of modified-Rh) or alcohols (in the case of modified-Co). The aldehydes/alcohols are then separated from paraffins in the stream. The resulting aldehydes/alcohols are in predominantly the 2C range.

The condensate products of iron catalysed high temperature Fischer-Tropsch reactions have relatively high concentration of olefins, relative to total volume of hydrocarbon products. Such high concentrations of olefins can be recovered economically by means of distillation or other separation techniques. However, when a relatively low concentration of olefins is produced, the cost of recovery thereof could even exceed the value generated by converting olefins to alcohols.

However, it has now surprisingly been found that alcohols and alkyl benzene can advantageously be co-produced from a Fischer-Tropsch derived feedstock, when the Fischer-Tropsch process is integrated with a hydroformylation and alkylation process.

It is an object of this invention to provide an improved method for the production of alcohols and alkyl benzene, typically those used as detergent precursors.

SUMMARY OF THE INVENTION

According to the invention there is provided a process for the production of aldehydes/alcohols and alkyl benzene, wherein:
  a hydrocarbon feed stream containing olefins and paraffins having an average number of carbon atoms from 10 to 18 per molecule, typically derived from the condensation product of a Fischer-Tropsch reaction, is subjected to a hydroformylation reaction to provide a hydroformylation product containing aldehydes/alcohols and paraffins,
  an aldehyde/alcohol product is separated from the paraffins in the hydroformylation product to provide an aldehyde/alcohol product stream and a paraffin stream;
  the paraffin stream separated from the hydroformylation product is subjected to a dehydrogenation reaction to form a dehydrogenation product containing olefins and paraffins; and
  the dehydrogenation product is subjected to an alkylation reaction to convert olefins to alkyl benzene.

The hydrocarbon feed stream typically contains olefins in which more than 5%, preferably more than 10%, more preferably more than 20%, by volume, of olefin molecules in the feed stream have a total number of carbon atoms which is different from the total number of carbon atoms of the most abundant two (preferably three) olefins (by carbon number) in the feed stream.

Preferably, the Fischer Tropsch reaction is a low temperature Fischer-Tropsch reaction with a reaction temperature below 280° C.

Preferably, the catalyst in the Fischer-Tropsch reaction is an iron based catalyst.

Preferably, hydrocarbon feed stream is a Fischer-Tropsch condensate product.

Preferably, oxygenates and/or acids are removed from the hydrocarbon feed stream, prior to introducing the stream to the hydroformylation reaction.

The aldehyde/alcohol product is preferably separated from the paraffins by azeotropic distillation in an azeotropic distillation column, wherein the solvent in the column is a mid-boiling polar entrainer.

The mid-boiling polar entrainer may be Indole, 2-Pyrrolidone, 1,6 Hexanediol, N-Aminoethyl-ethanolamine, 1,2-Benzenediol, N-methyl pyrrolidone (NMP), Ethylene carbonate, Propylene carbonate, Diethanolamine (DEA), or Diethylene glycol (DEG), preferably DEG.

Typically, the entrainer to feed ratio is from 1:05 to 1:3, preferably from 1:1 to 1:2, most preferably 1:1.8.

DESCRIPTION OF PREFERRED EMBODIMENTS

Figure 1:
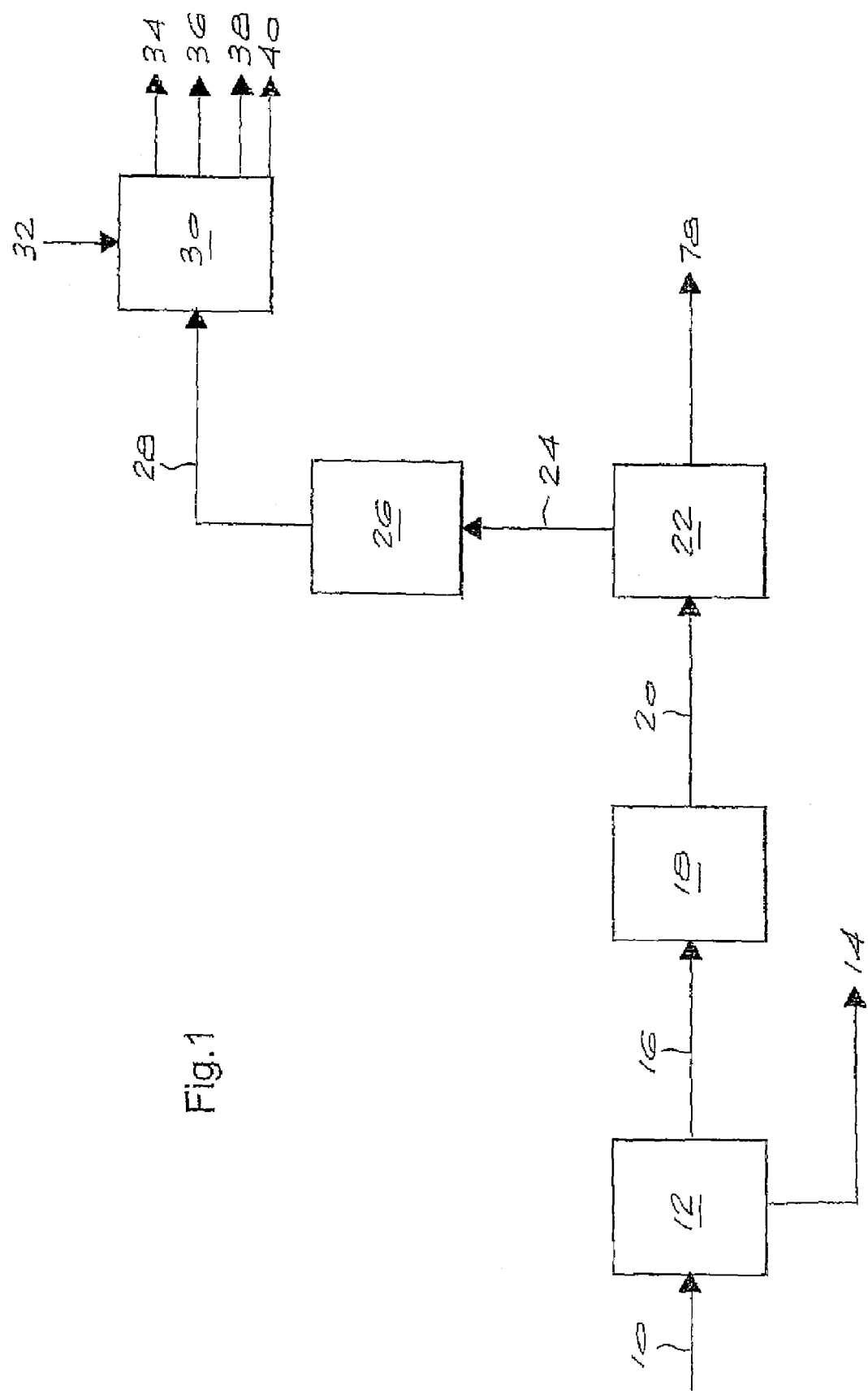
FIG. 1 is a block diagram of a process according to the invention.

A typical Fischer-Tropsch process involves the hydrogenation of CO in the presence of Group VIII metals, and includes, but is not limited to, Fe, Co, Mo, W, Rh, Pt, Pd Os, Ir and Ru. In principle, iron-based, cobalt-based or iron/cobalt-based Fischer-Tropsch catalysts can be used commercially in the Fischer-Tropsch reaction stage. Iron based catalysts are preferred for the present invention since they tend to produce a more olefinic hydrocarbon condensate product. In some embodiments, the iron-based Fischer-Tropsch catalyst may comprise iron and/or iron oxides which have been precipitated or fused. However, iron and/or iron oxides which have been sintered, cemented, or impregnated onto a suitable support may also be used. In some cases the iron based catalyst may contain various levels of promoters, the role of which may be to alter one or more of the activity, the stability, and the selectivity of the final catalyst. Preferred promoters are those influencing the surface area of the reduced iron ('structural promoters'), and these include oxides or metals of Mn, Ti, Mg, Cr, Ca, Si, Al, or Cu or combinations thereof. Preferred promoters for influencing product selectivities are alkali oxides of K and Na. Catalysts for the production of hydrocarbon species by a Fischer Tropsch process are generally known in the art.

The Fischer-Tropsch reaction may be effected in a fixed bed or preferably in a slurry phase reactor for low temperature Fischer-Tropsch applications, or in a fluidized bed reactor for high temperature Fischer-Tropsch applications. The Fischer-Tropsch reaction conditions may include utilizing a reaction temperature of between 190° C. and 340° C., with the actual reaction temperature being largely determined by the desired product spectrum. The products formed from this reaction are gaseous, liquid and optionally waxy hydrocarbons that include, inter alia, olefins and paraffins as well as oxygenates. The carbon number distribution of these products is generally described by the Anderson-Schulz-Flory distribution.

The low temperature Fischer-Tropsch (LTFT) process is a well known process in which synthesis gas, a mixture of gases including carbon monoxide and hydrogen, is reacted over a suitable catalyst to produce a mixture of straight and branched chain hydrocarbons ranging from methane to waxes with molecular masses above 1400 and smaller amounts of oxygenates (relative to high temperature Fischer-Tropsch). The LTFT catalyst may comprise active metals such as iron, cobalt, nickel or ruthenium and the catalyst will normally be a precipitated or supported catalyst.

Synthesis gas for the LTFT process may be derived from any carbon containing feedstock such as coal, natural gas, biomass or heavy oil streams. Some reactors for the production of heavier hydrocarbons using the LTFT process are slurry phase or tubular fixed bed reactors, while operating conditions are generally in the range of 180-280° C., in some cases in the 210-260° C. range, and 10-50 bar, in some cases between 20-30 bar. The molar ratio of hydrogen to carbon monoxide in the synthesis gas may be between 0.4 and 3.0, generally between 1.0 and 2.0.

As is the case with the LTFT process, the High Temperature Fischer-Tropsch (HTFT) process also makes use of the FT reaction albeit at a higher process temperature. A typical catalyst for HTFT process is iron based. Fused iron catalysts are best known in the prior art to be used in high temperature Fischer-Tropsch synthesis. Known reactors for the production of heavier hydrocarbons using the HTFT process are the circulating bed system or the fixed fluidized bed system, often referred to in the literature as Synthol processes. These systems operate at temperatures in the range 290-360° C., and typically between 320-350° C., and at pressures between 20-50 bar, in some cases between 20-30 bar. The molar ratio of hydrogen to carbon monoxide in the synthesis gas is essentially between 1.0 and 3.0, generally between 1.5 and 2.5. Generally, recycle streams are applied to increase the hydrogen content in the feed gas to the HTFT reactor to give a molar ratio of hydrogen to carbon dioxide at the reactor inlet of between 3.0 and 6.0 depending on the amount of carbon dioxide in the feed gas. Generally, a stoichiometric ratio, known as the Ribblett ratio $H_2/[2(CO)+3(CO_2)]=1.03$ is used as a target for the feed gas composition. Products from the HTFT process are all in the vapour phase at the reactor exit and are somewhat lighter than those derived from the LTFT process and, as an additional distinction, contain a higher proportion of unsaturated species and oxygenates.

The HTFT process is completed through various steps which include the preparation of synthesis gas ($H_2$ and CO) from any carbon containing feedstock such as by natural gas reforming or gasification of coal or other suitable hydrocarbonaceous feedstocks like petroleum based heavy fuel oils or biomass. This is followed by the HTFT conversion of synthesis gas in a reactor system like the Sasol Synthol or the Sasol Advanced Synthol reactor. One of the products from this synthesis is an olefinic distillate, also known as Synthol Light Oil (SLO).

Detailed descriptions of these two FT processes, LTFT and HTFT, may be found in "Fischer-Tropsch Technology", Studies in Surface Science and Catalysis, Vol. 152, Eds. A. P. Steynberg and M. E. Dry, Elsevier, 2004, amongst others.

With reference to FIG. 1, a Low Temperature Fischer-Tropsch reaction with a reaction temperature below 280° C., using an iron based catalyst, produces a hydrocarbon condensation product 10 which has been fractionated to contain olefins in which more than 5%, more than 10%, or more than 20%, by volume, of olefin molecules in the feed stream have a total number of carbon atoms which is different from the total number of carbon atoms of the most abundant two (preferably three) olefins (by carbon number) in the feed stream. The fractionated hydrocarbon stream 10 containing olefins in a 3C range or greater, typically in a 4C range, such as C11-C14 olefins (for example containing approximately 37% C11, 30% C12, 18% C13, and 11% C14 olefins, by volume of the total olefins in the stream) is introduced to a oxygenate removal step 12 in which oxygenates 14 are removed from the stream. This oxygenate removal step is important because it reduces the acid content of the stream (which is necessary for the following hydroformylation reaction) and the removal of oxygenates is important for the following alkylation reaction. The oxygenate removal step may be achieved using Liquid-Liquid Extraction (e.g. acetonitrile/water or methanol/water), dehydration or hydrogenation.

From the oxygenate removal step 12, a feed stream 16 containing paraffins and linear olefins is introduced to a hydroformylation reactor 18. In the hydroformylation reactor 18, olefins in the stream are subjected to the "Oxo" process. In the Oxo process, olefins are reacted with carbon monoxide and hydrogen in the presence of a catalyst (typically rhodium or cobalt catalyst) to form aldehydes, which are then hydrogenated to alcohols. In the Oxo process, the carbon number of the olefins is increased by 1 and a hydroxyl group is added to form the alcohols.

Hydroformylation (Oxo) processes for the production of oxygenated products, particularly aldehydes and/or alcohols, by the reaction of an olefinic feedstock with carbon monoxide and hydrogen at elevated temperatures and pressures in the presence of hydroformylation catalysts, are well known. The alcohols and/or aldehydes that are produced in these processes generally correspond to the compounds obtained, in the hydroformylation reaction, by the addition of a carbonyl or carbinol group to an olefinically unsaturated carbon atom in the feedstock with simultaneous saturation of the olefin bond. A hydroformylation catalyst is selected according to the particular oxygenated products which are required from a particular olefinic feedstock. Thus, a hydroformylation catalyst may typically include a Group VIII metal for example, but not limited to cobalt, rhodium, platinum and palladium. In some embodiments, the metal may be combined with a ligand for example, but not limited to a phosphine and/or phosphite ligand. Examples of such catalysts are triphenyl phosphine ligands used with rhodium, and alkyl phosphine ligands used with cobalt.

Hydroformlyation may be conducted as a batch process, continuous process or semi-continuous process. For ligand modified cobalt catalysts, typical hydroformylation temperatures are between 140° C. and 210° C. and preferably between 160° C. and 200° C. Synthesis gas (syngas) composition with respect to the $H_2$:CO ratio may be 1:2-3:1 and preferably about 2:1; syngas pressure may typically be 20-110 bar and preferably 50-90 bar, the molar ratio of ligand to metal may typically be 10:1-1:1 and preferably is 1:1-3:1 and the % metal to olefin by mass may typically be 0.1-1 and preferably is 0.2-0.7. For ligand modified rhodium catalysts, typical hydroformylation temperatures are between 50° C. and 150° C. and preferably between 80° C. and 130° C. Syngas composition with respect to the H2:CO ratio may be 1:2-3:1 and preferably about 1.1-1.2; syngas pressure may typically be 2-60 bar and preferably 5-30 bar and the % metal to olefin by mass may typically be 0.001-0.1 and preferably is 0.01-0.05.

Paraffins in the feed stream 16 are inert in the Oxo process and pass through the hydroformylation reactor 18 unchanged. Some hydrogenation of olefins to paraffins also occurs. In the case of a $C_{11}$-$C_{14}$ feed stream 16, linear alcohols in the $C_{12}$-$C_{15}$ range are formed in the hydroformylation reactor 18, and a stream 20 containing alcohols in the $C_{12}$-$C_{15}$ range and paraffins in the $C_{11}$-$C_{14}$ range exits from the hydroformylation reactor 18. The streaming contain alcohols in which more than 5%, more than 10%, or more than 20%, by volume, of alcohol molecules in the stream 20 have a total number of carbon atoms which is different from the total number of carbon atoms of the most abundant two (or three) alcohols (by carbon number) in the feed stream.

The separation of alcohols from paraffins in such a wide range as that present in the stream 20 is problematic because of the overlapping boiling points of the heavy paraffins and light alcohols.

Figure 2:
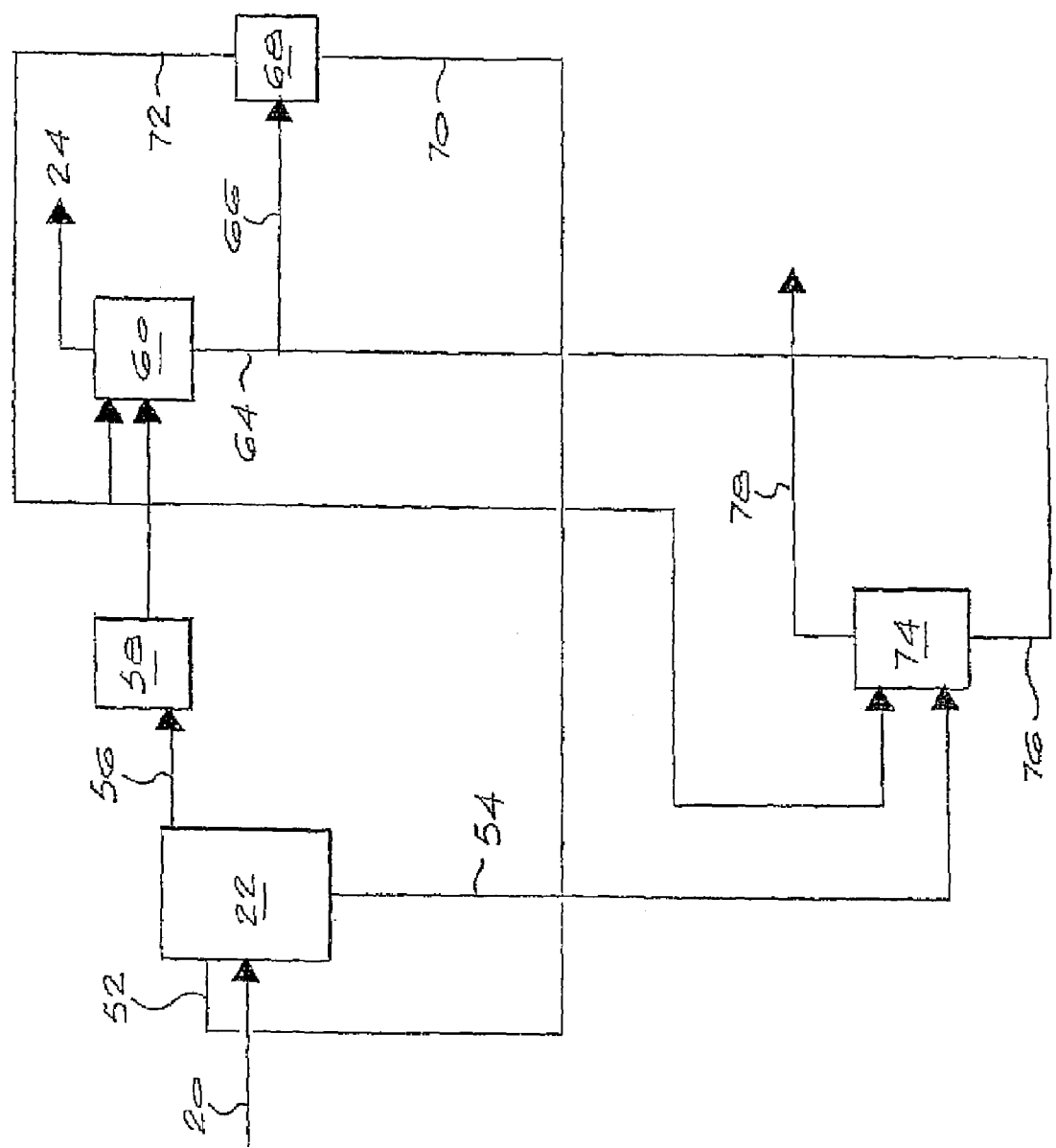
FIG. 2 is a block diagram of a process for azeotropic distillation that may be used in the process depicted in FIG. 1.

Nevertheless, it has been found that it is possible to effect such a separation by introducing the stream 20 to an azeotropic distillation column 22. Azeotropic distillation is the use of an additional component that forms an azeotrope with one or more of the feed components to a distillation column and thereby enhancing the relative volatility towards the desired separation. A method of effecting the separation of alcohols from paraffins to form a stream 24 containing paraffins in the $C_{11}$-$C_{14}$ range and a stream 78 containing a detergent range alcohol product in the $C_{12}$-$C_{15}$ range is described, with reference to FIG. 2, below:

The azeotropic distillation column 22 is supplied with a mid-boiling polar entrainer 52 at the top of the column 22, and the hydrocarbon stream 20 is supplied to the column 22, mid-way along the column 22. The azeotropic distillation column 22 operates at approx. 15-30 kPa abs. The column is typically operated under vacuum to limit the bottoms temperature to about 200° C.; the preferred pressure range is about 15-30 kPa abs. The optimum number of theoretical stages in this column is approximately 30-35. A mid-boiling polar entrainer is a solvent that has a boiling point between the lowest and highest boiling components in the feed to be separated. It is found that mid-boiling entrainers are more effective compared with low-boiling entrainers or high-boiling solvents because the mid-boiling polar entrainer is selected to distribute from a bottoms stream 54 to an overhead stream 56 of the azeotropic distillation column 22, thereby ensuring that the enhancement of relative volatility occurs over the entire column 22. N-methyl pyrrolidone (NMP) and diethylene glycol (DEG) are suitable mid-boiling entrainers such as Indole, 2-Pyrrolidone, 1,6 Hexanediol, N-Aminoethyl-ethanolamine, 1,2-Benzenediol, N-methyl pyrrolidone (NMP), Ethylene carbonate, Propylene carbonate, Diethanolamine (DEA), or Diethylene glycol (DEG), with DEG being preferred. The addition of DEG leads to the formation of azeotropes with both $C_{14}$ and $C_{12}OH$, but there is a larger boiling point difference of about 13° C. between these new azeotropes which increases the relative volatility between the $C_{14}$ and $C_{12}OH$. The boiling point of DEG is about 245° C. A similar effect was observed using NMP, but more NMP is required to achieve the same separation. The boiling point of NMP is 204° C. Typically, the entrainer 52 to feed 20 ratio is from 1:05 to 1:3, preferably from 1:1 to 1:2, most preferably 1:1.8. According to the process of the invention, the overhead stream 56 from the distillation column 22, containing olefins and mid-boiling polar entrainer, is introduced to a condenser 58 and then to a decanter 60, where a paraffin product 24 is separated in a water wash from the mid-boiling polar entrainer 64. The separated mid-boiling entrainer is then sent via a line 66 to a solvent dryer 68. Dried polar entrainer 70 from the solvent dryer 68 is recycled to the azeotropic distillation column 22. Water 72 from the solvent dryer 68 is conveniently recycled to the Decanter 60. The bottoms stream 54 from the azeotropic distillation column 22, which contains some of the mid-boiling entrainer and alcohols is washed with water in a wash column 74 which is conveniently supplied with water from the water recycle stream 72. A water-phase 76 containing the entrainer is sent to the solvent dryer 68 via the line 66. An alcohol product stream 78 containing $C_{12}$-$C_{15}$ alcohols is obtained from the wash column 74.

Referring back to FIG. 1, the stream 24 containing paraffins in the $C_{11}$-$C_{14}$ range is sent to a dehydrogenater 26 to convert linear paraffins into linear olefins. In the present case, the UOP Pacol™ dehydrogenation technology is used for activation of the paraffins. Typically, the dehydrogenation reaction is carried out at 400-500° C. and 300 kPa (abs), in the presence of a modified platinum catalyst on an aluminium oxide substrate. Conversion of paraffins to olefins is limited to 10-15% in order to limit further dehydrogenation of mono-olefins to dienes and cyclics. UOP's DEFINE™ and PEP™ processes are used to further remove unwanted by-products from the pacolate, that are formed during dehydrogenation. The DEFINE™ process selectively hydrogenates dienes to the mono-olefins, whilst PEP™ removes cyclic compounds from the pacolate.

An olefin-paraffin stream 28 from the dehydrogenation reactor 26 is introduced into an alkylation reactor 30 which is also supplied with benzene 32. An alkylation reaction in the alkylation reactor 30 may be carried out by using a Friedel-Crafts type condensation catalyst such as $AlCl_3$, $H_2SO_4$, $BF_3$, HF or a solid acid catalyst. In the present case, the UOP DETAL™ solid acid catalyst alkylation technology is used. Typically, the alkylation reaction is carried out at a temperature of greater than 100° C. and a pressure of about 300 kPa (abs), in the presence of UOP's proprietary DETAL™ catalyst (see Smith R. (1991) Linear alkylbenzene by heterogeneous catalysis. PEP Review No. 90-2-4, SRI International). The olefins from the olefin paraffin feed 28 react with the benzene 32 in the alkylation reactor 30 to provide a $C_{11}$-$C_{14}$ linear alkyl benzene product 34, unreacted paraffins 36, unreacted benzene 38, and a heavies stream 40. The unreacted benzene 38 is recycled to the alkylation reactor 30. The unreacted paraffin 36 may be recovered as a product or it may be recycled to the dehydrogenation reactor 26.

In another embodiment of the invention, the oxygenate removal step 12 may be replaced with an acid removal step. However, an oxygenate removal step will then be required on the stream 24 or 28 before the alkylation reaction step 30.

In a further embodiment of the invention, a preferred $C_{10}$-$C_{13}$ linear alkylbenzene product 34 may be obtained by fractionating the stream 24 into the $C_{11}$-$C_{13}$ range and adding a $C_{10}$ paraffin containing material prior to the dehydrogenation reactor 26.

In an alternative process, two separate hydrocarbon streams which are the product of a Fischer-Tropsch reaction, each containing hydrocarbons in a 2C range, for example a $C_{11}$-$C_{12}$ and a $C_{13}$-$C_{14}$ stream, are reacted in separate hydroformylation reactors, the separated paraffins are combined to form a $C_{11}$-$C_{14}$ stream which is then subjected to the rest of the steps of the process of the invention to produce a linear alkyl benzene product. An advantage of this embodiment is that the separation step of alcohols from paraffins after the hydroformylation reaction is simplified because of the narrower carbon range, and there is no overlap in the boiling points of the alcohols and inert paraffins. The draw-back is an increase in capital expenditure because the process requires two separate hydroformylation reactors.

The simultaneous production of detergent alcohols and linear alkyl benzene of the invention achieves economies of scale that make the process more commercially viable. The process also permits flexibility to change the products between detergent alcohols and linear alkyl benzene, depending on demand.

The invention claimed is:

1. A process for the co-production of aldehydes/alcohols and alkyl benzene, wherein:
    a hydrocarbon feed stream containing olefins and paraffins having an average number of carbon atoms from 10 to 18 per molecule is subjected to a hydroformylation reaction to provide a hydroformylation product containing aldehydes/alcohols and paraffins;
    an aldehyde/alcohol product is separated from the paraffins in the hydroformylation product to provide an aldehyde/alcohol product stream and a paraffin stream;
    the paraffins separated from the hydroformylation product are subjected to a dehydrogenation reaction to form a dehydrogenation product containing olefins and paraffins; and
    the dehydrogenation product is subjected to an alkylation reaction to convert olefins to alkyl benzene.

2. The process as claimed in claim 1, wherein more than 5% by volume of olefin molecules in the hydrocarbon feed stream have a total number of carbon atoms which is different from the total number of carbon atoms of the most abundant two carbon numbers of olefins in the hydrocarbon stream.

3. The process as claimed in claim 2, wherein more than 10% by volume of olefin molecules in the hydrocarbon feed stream have a total number of carbon atoms which is different from the total number of carbon atoms of the most abundant two carbon numbers of olefins in the hydrocarbon stream.

4. The process as claimed in claim 3, wherein more than 20% by volume of olefin molecules in the hydrocarbon feed stream have a total number of carbon atoms which is different from the total number of carbon atoms of the most abundant two carbon numbers of olefins in the hydrocarbon stream.

5. The process as claimed in claim 1, wherein the hydrocarbon feed stream is derived from the product of a low temperature Fischer-Tropsch reaction with a reaction temperature below 280° C.

6. The process as claimed in claim 5, wherein the catalyst in the Fischer-Tropsch reaction is an iron based catalyst.

7. The process as claimed in claim 5, wherein the hydrocarbon feed stream is a condensate product from the Fischer-Tropsch reaction.

8. The process as claimed in claim 1, wherein oxygenates and/or acids are removed from the hydrocarbon feed stream, prior to introducing the stream to the hydroformylation reaction.

9. The process as claimed in claim 1, wherein the aldehyde/alcohol product is separated from the paraffins by azeotropic distillation in an azeotropic distillation column, wherein the solvent in the column is a mid-boiling polar entrainer.

10. The process as claimed in claim 9, wherein the mid-boiling polar entrainer is Indole, 2-Pyrrolidone, 1,6 Hexanediol, N-Aminoethyl-ethanolamine, 1,2-Benzenediol, N-methyl pyrrolidone (NMP), Ethylene carbonate, Propylene carbonate, or Diethanolamine (DEA), or Diethylene glycol (DEG).

11. The process as claimed in claim 10, wherein the mid-boiling polar entrainer is DEG.

12. The process as claimed in claim 10, wherein the entrainer to feed ratio in the azeotropic distillation column is from 1:05 to 1:3.

13. The process as claimed in claim 12, wherein the entrainer to feed ratio in the azeotropic distillation column is from 1:1 to 1:2.

14. The process as claimed in claim 13, wherein the entrainer to feed ratio in the azeotropic distillation column is 1:1.8.

* * * * *